US010983123B2

(12) United States Patent
Lakshmipathy et al.

(10) Patent No.: US 10,983,123 B2
(45) Date of Patent: Apr. 20, 2021

(54) MARKERS CAPABLE OF DISTINGUISHING CELL PLURIPOTENCY AND USES THEREOF

(71) Applicant: LIFE TECHNOLOGIES CORPORATION, Carlsbad, CA (US)

(72) Inventors: Uma Lakshmipathy, Carlsbad, CA (US); Rene Quintanilla, Temecula, CA (US); Joanna Asprer, Glendale, CA (US)

(73) Assignee: Life Technologies Corporation, Carlsbad, CA (US)

( * ) Notice: Subject to any disclaimer, the term of this patent is extended or adjusted under 35 U.S.C. 154(b) by 246 days.

(21) Appl. No.: 16/047,504

(22) Filed: Jul. 27, 2018

(65) Prior Publication Data
US 2019/0064164 A1   Feb. 28, 2019

Related U.S. Application Data

(62) Division of application No. 14/433,590, filed as application No. PCT/US2013/031639 on Mar. 14, 2013, now Pat. No. 10,073,096.
(Continued)

(51) Int. Cl.
*G01N 33/569* (2006.01)
*C12N 5/0775* (2010.01)
(Continued)

(52) U.S. Cl.
CPC ..... *G01N 33/56966* (2013.01); *C12N 5/0081* (2013.01); *C12N 5/0656* (2013.01);
(Continued)

(58) Field of Classification Search
CPC ....... G01N 33/56966; G01N 2333/705; G01N 2333/70585; C12N 5/0081; C12N 5/0656; C12N 5/0662
See application file for complete search history.

(56) References Cited

U.S. PATENT DOCUMENTS 9,617,513 B2 *  4/2017  Young ................. C12N 5/0607
10,073,096 B2 *  9/2018  Lakshmipathy ..........................
                                             G01N 33/56966
(Continued)

FOREIGN PATENT DOCUMENTS

| JP | 2005 204590 | * 8/2005 | ............... C12N 5/06 |
|----|-------------|----------|---------------------------|
| JP | 2005-204590 | 8/2005 | |
| WO | WO-2014/055121 | 4/2014 | |

OTHER PUBLICATIONS

Nakamura Kimitoshi (JP 2005 204590) Aug. 2005—machine translation.*

(Continued)

*Primary Examiner* — Gailene Gabel

(57) ABSTRACT

Provided herein are compositions, methods and uses that relate to or result from the identification of markers that can distinguish between cells at different stages of pluripotency. Certain embodiments provide markers that can distinguish between parental cells (i.e. differentiated cells), partially pluripotent (i.e. partially reprogrammed) and pluripotent (i.e. fully reprogrammed cells). Also provided here are uses of such differential markers, for example, in identification of cell potential, in diagnostics, in differential separation, and in creating efficient workflows that involve fewer steps and lesser time in identifying or separating a desired reprogrammed clone or cell line from a mixture of cells at various stages of pluripotency. In certain embodiments, the activity of these markers can be manipulated to influence cell potential for research or medical purposes.

11 Claims, 13 Drawing Sheets

Related U.S. Application Data

(60) Provisional application No. 61/725,886, filed on Nov. 13, 2012, provisional application No. 61/710,205, filed on Oct. 5, 2012.

(51) Int. Cl.
  *C12N 5/00* (2006.01)
  *C12N 5/077* (2010.01)

(52) U.S. Cl.
  CPC ..... *C12N 5/0662* (2013.01); *G01N 2333/705* (2013.01); *G01N 2333/70585* (2013.01)

(56) References Cited

U.S. PATENT DOCUMENTS

| | | |
|---|---|---|
| 2010/0003752 A1 | 1/2010 | Herrera Sanchez et al. |
| 2011/0306516 A1 | 12/2011 | Kahler et al. |

OTHER PUBLICATIONS

Dubois, et al., "SIRPA is a specific cell-surface marker for isolating cardiomyocytes derived from human pluripotent stem cells", *Nature Biotechnology*, vol. 29, No. 11, Nov. 2011, 1011-1019.

Miltenyi Biotec, "Pluripotent Stem Cell Isolation Kit (130-095-267)", 2010, 1-3.

PCT/US2013/031639, "International Search Report and Written Opinion dated", Sep. 4, 2013, 1-15.

PCTUS2013/031639, "International Preliminary Report on Patentability and Written Opinion dated", Apr. 26, 2015, 1-10.

PCTUS2013/031639, "Partial Search Report dated", Jun. 11, 2013, 1-8.

Soldner, et al., "Parkinson's Disease Patient-Derived Induced Pluripotent Stem Cells Free of Viral Reprogramming Factors", *Cell*, vol. 136, Mar. 6, 2009, 964-977.

Sun, et al., "Feeder-free derivation of induced pluripotent stem cells from adult human adipose stem cells; and Supporting Information", *Proceedings of the National Academic of Sciences*, vol. 106, No. 37, Sep. 15, 2009, 1-11 (15720-15725).

Ward, et al., "The 5T4 oncofoetal antigen is an early differentiation marker of mouse ES cells and its absence is a useful means to assess pluripotency", *Journal of Cell Science*, vol. 116, No. 22, Nov. 15, 2003, 4533-4542.

Yuan, et al., "Cell-Surface Marker Signatures for the Isolation of Neural Stem Cells, Glia and Neurons Derived from Human Pluripotent Stem Cells", *PLoS One*, vol. 6, No. 3, Mar. 2011, e17540 (1-16).

\* cited by examiner

Experimental confirmation of CD44 differential pattern staining of parental fibroblasts and iPSCs Experimental confirmation of CD44 differential pattern between MEF feeders and iPSCs CD44 Antibody-AF488 staining of MEF alone (left panel) and H9 ESC cultured on MEFS (right panel)

FACS analysis of CD44 Antibody-AF488 stained MEF alone and H9 ESC cultured on MEF Comparison of expression with CD271

MARKERS CAPABLE OF DISTINGUISHING CELL PLURIPOTENCY AND USES THEREOF

CROSS-REFERENCE TO RELATED APPLICATIONS

This application is a divisional of U.S. application Ser. No. 14/433,590, filed Apr. 3, 2015, now U.S. Pat. No. 10,073,096, which is a National Stage Entry of International Application No. PCT/US2013/031639, filed Mar. 14, 2013, and claims the benefit of priority to U.S. Provisional Application No. 61/725,886 filed Nov. 13, 2012 and U.S. Provisional Application No. 61/710,205 filed Oct. 5, 2012, which disclosures are herein incorporated by reference in their entirety.

TECHNICAL FIELD

The present invention relates to life sciences and medical sciences. In certain embodiments, the invention relates to markers capable of identifying cells based on their level of pluripotency and methods and compositions based on the identification and/or use and/or manipulation of these markers.

BRIEF DESCRIPTION OF THE FIGURES

The following figures, which are described below and which are incorporated in and constitute a part of the specification, illustrate exemplary embodiments that are not to be considered limiting to the scope of the invention.

FIG. 7 shows a comparative analysis of expression of three genes: a housekeeping gene (left), CD13 (right) and CD 44 (middle) in BJ fibroblasts, H9 ESCs, iPSCs and partially reprogrammed iPSCs. CD44 was highly expressed in BJ fibroblasts and partially reprogrammed iPSCs, but was poorly expressed in H9 ESCs and iPSCs (fully reprogrammed cells). Correspondingly, marker CD13 showed poor expression in partially reprogrammed iPSCs, H9 ESCs and iPSCs thereby indicating that the marker CD13 cannot clearly distinguish between partial and fully pluripotent cells.

FIG. 8A shows that the expression of the CD271 market is not high enough in fibroblast compared to pluripotent cells to be significant. FIG. 8B shows that CD44 was highly expressed in BJ fibroblasts and in partially reprogrammed iPSCs (par iPSC), but was poorly expressed in H9 ESCs and in iPSCs. Correspondingly, marker CD271 showed equivalent expression in parental cells, H9 ESCs, partially reprogrammed iPSCs (par iPSCs), and iPSCs (see panel 8(B)), thereby indicating that the CD271 marker cannot clearly distinguish between parental, partial and fully pluripotent cells.

DETAILED DESCRIPTION

Definitions

Figure 1A:
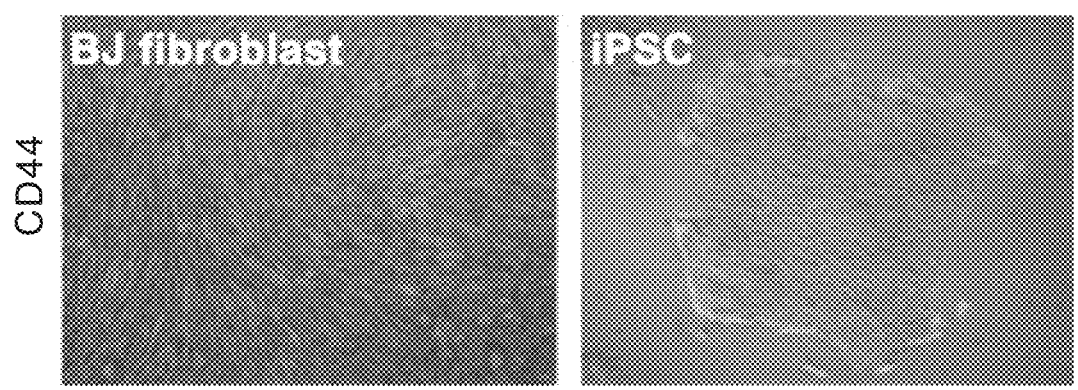
FIG. 1(A) shows the fluorescent staining of human BJ fibroblast (left panel) and iPSC derived from BJ fibroblasts (right panel) with Alexa Fluor 488 (AF488) dye labeled conjugate CD44 antibody (Life Technologies, CA, USA).

"Embryonic stem cells" (ESCs) are undifferentiated cells found in early embryos, and typically are derived from a group of cells called the inner cell mass, a part of the blastocyst. Embryonic stem cells are self-renewing and can form all specialized cell types found in the body (they are pluripotent). ESCs include ECSs of human origin (hESCs) and ESCs of non-human or animal origin. ESCs can typically be propagated, under appropriate conditions, without differentiation, due to their self-renewing properties.

"Pluripotent" or "multipotent" stem cells as used herein, have the ability to develop into more than one cell type of the body. However, pluripotent cells generally cannot form "extra-embryonic" tissues such as the amnion, chorion, and other components of the placenta. "Pluripotency" may be assessed by the "puritest" (Scripps Research team), a microarray technology based test that provides a detailed molecular model for a normal pluripotent stem cell line. Alternately, it can be done by showing the ability of the pluripotent cell to generate a teratoma after injection into an immunosuppressed mouse (the teratoma assay).

Reprogramming may be done for any reason, for example, to achieve a less differentiated status in certain instances, or a more differentiated status, or for directed differentiation. That is, reprogramming could be done to alter the differentiation capacity of a cell. In certain instances, "reprogramming" may use one or more stem cell marker genes (i.e. "reprogramming factors") like Oct4 (also termed Oct-3 or Oct3/4), Sox2, c-Myc, Klf4, Oct3/4, Nanog, SSEA1 (Stage Specific Embryonic Antigens), TRA1-80, etc. to reprogram a somatic or an adult cell towards a less differentiated status.

"Partially reprogrammed cell," or "quasi-reprogrammed cell," is defined as a somatic or adult cell which, although exposed to exogenous factors to induce an ESC like stage, does not demonstrate the full range of endogenous pluripotent markers, either at the molecular or cellular level, and does not have the potential to differentiate in vivo or in vitro into cells typical for the three germ layers: endoderm, mesoderm, and ectoderm. Typically, these cells can revert back to their starting somatic cell type, or continue to express a cellular marker or molecular signatures of the starting cell type. Another way to describe a partially reprogrammed cell may be as a cell that is not fully pluripotent, but not entirely somatic, and is at a stage somewhere in between somatic and fully pluripotent. For example, a partially reprogrammed cell may express some markers associate with pluripotency but yet may not form embryoid bodies (i.e. will not be able to randomly differentiate). For example, a partially reprogrammed cell may further or alternatively have methylation patterns reminiscent of its parental cell type that would be lost or lessened in a more fully reprogrammed cell. In one embodiment, a partially reprogrammed cell may be defined as a cell expressing at least one of the following markers: beta 2 microglobulin, endosialin, CD44, cadherin 11 and colectin 12, just as the parental somatic cell. In a particular embodiment, a partially reprogrammed cell may be defined as a cell expressing, or robustly expressing, or highly expressing the CD44 marker.

"Fully reprogrammed cell" is defined as a somatic or adult cell which has demonstrates the ability to propagate indefinitely while maintaining a stable karyotype. These cells continue to express typical ESC like morphologies and cellular and molecular signatures of pluripotency. They also demonstrate the ability to differentiate into cells typical of the three embryonic germ layers and demonstrate an ESC like molecular phenotype. In one embodiment, a fully reprogrammed cell may be defined as a cell not expressing, or negligibly expressing, or poorly expressing at least one of the following markers: beta 2 microglobulin, endosialin, CD44, cadherin 11 and colectin 12, compared to a parental somatic cell. In a particular embodiment, a fully reprogrammed cell may be defined as a cell not expressing, or negligibly expressing, or poorly expressing the CD44 marker.

"Somatic stem cells" are non-embryonic stem cells that are not derived from gametes (egg or sperm cells). These somatic stem cells may be of fetal, neonatal, juvenile or adult origin.

DESCRIPTION

Human fibroblasts are the most common somatic cell type used for reprogramming. In order to address the current challenge in the stem cell workflow where scientists have to differentiate between parental fibroblasts, partially reprogrammed fibroblasts and fully reprogrammed iPSCs (and ESCs or pluripotent cells), anew marker was identified by comparative global transcriptome analysis of parental fibroblasts, ESCs and iPSCs. As discussed in detail in the examples below, the property of an exemplary marker such as the CD44 marker, in clearly distinguishing or identifying pluripotent cells over feeder layer cells like mouse embryonic fibroblasts (MEFs), or in distinguishing parental mesenchymal and partially reprogrammed mesenchymal cells from fully reprogrammed mesenchymal cells fulfills an unmet need in an important part of the stem cell workflow. In its broadest aspect, the ability of markers such as beta 2 microglobulin, endosialin, CD44, cadherin 11 and colectin 12, etc. to clearly distinguish pluripotent cells from non-pluripotent and/or partially pluripotent cells is useful for developing tools used, for example, during a reprogramming experiment, and helps an unmet need of quickly or accurately identifying pluripotent cells from a mixture of a variety of cells at various stages of reprogramming.

In a reprogramming experiment, cells generally proceed from a differentiated state to a partially differentiated state to a pluripotent state. By using markers identified in this disclosure, one of skill in the art would be able to monitor the journey of a cell along its path, possibly in either direction (towards differentiation or dedifferentiation), based on the appearance and/or disappearance of one or more candidate markers identified herein.

In one embodiment, CD44 was identified as a suitable pluripotent marker as it is highly expressed in mouse and human fibroblasts and in partially reprogrammed fibroblasts, but is negligible or absent in ESCs and iPSCs, thus making it a good differential marker that can distinguish between these cell types. This differential profile of CD44 was further exploited to identify and separate a fully reprogrammed cell from a mixture of parental fibroblast and partially reprogrammed fibroblasts, using an anti-CD44 antibody attached to a bead or a solid support. Such quick and efficient separation techniques enable cleaner reprogrammed cell preparations particularly needed for downstream clinical applications. This technology can also be used, for example, to monitor differentiation in real-time by utilizing a fluorescent stain, or a live stain and the monitoring of progression through the various stages of differentiation. In certain embodiments, markers such as CD44 may identify specific stages of a reprogramming workflow based, for example, on its expression (or level of expression) or absence of expression during reprogramming.

Besides distinguishing between partially and fully reprogrammed cells, another useful application of CD44 differential expression is in MEF co-culture systems. In current feeder-dependent culture systems, PSCs, ESCs and iPSCs are co-cultured on a mitotically inactivated feeder layer of mouse embryonic fibroblasts (MEF). MEFs are then separated from the final desired ESC or iPSC cell products by sequential passaging to get rid of the MEFs. This takes enormous time and resources and is tedious. Described herein are methods to perform a quick and single step separation technique of MEFs from iPSCS or ESCs. Based on the observation that CD44 is highly expressed in MEFs but not (or negligibly) in iPSCs and ESCs, the unwanted MEFs can be quickly eliminated from a preparation of fully reprogrammed fibroblast cells by using, for example, an anti-CD44 antibody linked bead or solid support.

Other mesenchymal markers were also identified by comparative global transcriptome analysis of parental fibroblasts, ESCs and iPSCs and are shown in Table 1 and discussed in Example 1.

In its broadest embodiment, the ability of markers such as beta 2 microglobulin, endosialin, CD44, cadherin 11 and colectin 12, etc. to clearly distinguish pluripotent cells from non-pluripotent and/or partially pluripotent cells forms the basis for the development of compositions and methods for distinguishing between the above cells in a mixed cell population, or compositions and methods to separate one of more of the above cells from the rest of the cell mixture, or compositions and methods of evaluating agents that may modulate reprogramming by treating a somatic cell preparation with the agent for a sufficient time to permit (or inhibit) reprogramming; or compositions and methods of evaluating agents that may modulate differentiation by treating a pluripotent cell preparation with the agent for a sufficient time to permit (or inhibit) differentiation; staining the somatic cell preparation with an anti-CD44 antibody; and identifying a cell that shows a lack of staining with the anti-CD44 antibody. In some embodiments, a ligand is generated to a marker. In some embodiments, and in many exemplary embodiments described herein, the ligand is an antibody. However, as would be known by one of skill in the art, ligands other than antibodies will be substitutable in depending on the situation.

In some embodiments, this difference in marker expression may be applied to various mammalian cells, such as cells from mouse, humans, rats, guinea pigs, primates, pig, dog, etc. In a particular embodiment, this difference can be applied to specific types of cells, for example, mesenchymal cells, and more particularly to cells such as fibroblasts, adipocytes, blood cells, etc. In certain embodiments, this differential expression can be harnessed to develop tools that aid in the elimination, for example, of MEFs from ESC and iPSC culture, or for the generation of a more homogeneous ESC/iPSC (or pluripotent) populations for downstream applications using, for example, Dynal® MyOne™ Streptavidin magnetic beads to bind to biotin labeled CD44 antibody and pulling away unwanted MEF or non-reprogrammed or partially reprogrammed cells away thus forming a more homogeneous population of pluripotent cells (i.e. ESCs or iPSCs etc.). In other embodiments, any CD44-specific ligand system can be used to separate MEF cells or non-reprogrammed or partially reprogrammed cells to form a more homogeneous population of pluripotent cells (i.e. ESCs or iPSCs etc.). In one embodiment, this (or other methods and compositions described herein) are applied to cells during or after the transdifferentiation process.

In another embodiment, CD44 differential staining can be used during early reprogramming to better identify unreprogrammed, partially reprogrammed and fully reprogrammed colonies by using an anti-CD44=fluorescent labeled antibody. In further embodiments, additional uses of markers such as CD44 in stem cell applications could include: (i) any marker—antibody coated Dynal beads (such as, anti-CD44 antibody coated magnetic beads) to capture epithelial cells from body fluids such as blood, saliva, urine etc. as a noninvasive method for cell collection for genetic analysis, forensic analysis, clinical analysis, etc., or for any use where somatic cells are necessary for reprogramming; (ii) creation of a suspension, feeder-dependent ESCs or iPSC culture system by immobilizing anti-marker antibody (such as, antiCD44 antibody coated on any bead) and capturing inactivated MEF cells on the beads to create a MEF suspension bead system for ESCs or iPSC culture; (iii) creating an efficient way to generate conditioned media by using an ESCs or iPSC suspension culture system described above in (ii); (iv) identifying and evaluating a test agent that may enhance or regress differentiation.

To identify an agent that causes or regresses or turns back differentiation, an exemplary workflow may involve using a fluorescent labeled or live stain-labeled antibody directed to a differential marker such as, for example, CD44 to identify and visualize partial and/or fully differentiated cells in real time after treatment with the test or candidate agent. One of skill in the art would know, based on the teachings of this disclosure, to follow somatic cell dedifferentiation or stem cell differentiation, or, to follow the progression of a stem cell through various stages of differentiation to a pluripotent cell, such as, through partial pluripotency, finally to a fully pluripotent cell (and vice versa), with or without treatment with a test agent. Using such methods, agents capable of increasing/decreasing the efficiency, speed and quality of differentiation may be identified.

In one embodiment, a method is described for identifying a pluripotent cell within a mixture of cells, the method comprising contacting the mixture of cells with an antibody wherein the antibody has the capacity to bind a differentiated cell or a partially reprogrammed cell but does not bind the pluripotent cell; visualizing the antibody; and identifying the pluripotent cell based on the lack of antibody binding. In one embodiment, the antibody is directed towards CD44, beta 2 microglobulin, endosialin, cadherin 11 or colectin 12. In one embodiment, the antibody is directed towards CD44.

In one embodiment, the antibody is linked to a marker that allows direct visualization. In one embodiment, the method further comprises identifying the differentiated cell or the partially reprogrammed cell based on antibody binding. In one embodiment, the mixture of cells is evaluated or characterized based on the proportion of pluripotent, differentiated and partially reprogrammed cells in the mixture.

In one embodiment, a method is described for identifying a differentiated cell or a partially reprogrammed cell within a mixture of cells, the method comprising contacting the mixture of cells with an antibody wherein the antibody has the capacity to bind a differentiated cell or a partially reprogrammed cell but does not bind the pluripotent cell; visualizing the antibody; and identifying the differentiated cell or the partially reprogrammed cell based on antibody binding wherein the antibody is directed towards CD44, beta 2 microglobulin, endosialin, cadherin 11 or colectin 12.

In one embodiment, a method is described for evaluating the ability of an agent to affect the progress of a cell from a differentiated or partially reprogrammed state to a pluripotent state, the method comprising identifying the pluripotency state of the cell in the presence of the agent and comparing the result to that seen in the absence of the agent.

In one embodiment, a method is described for evaluating the ability of an agent to affect the progress of a cell from a pluripotent state to a differentiated or partially differentiated state, the method comprising identifying the pluripotency state of the cell in the presence of the agent and comparing the result to that seen in the absence of the agent.

In one embodiment of the described methods, the cell is a mammalian cell. In one embodiment, the cell is, for example, human, mouse, rat, monkey, pig, dog, or guinea pig.

In one embodiment, a method is described for separating a pluripotent cell from a mixture comprising the pluripotent cell and a differentiated cell or a partially reprogrammed cell or both, the method comprising contacting the mixture of cells with an antibody wherein the antibody is bound to a solid surface; separating the pluripotent cell from the mixture based on it not binding to the solid surface wherein the antibody is directed towards CD44, beta 2 microglobulin, endosialin, cadherin 11 or colectin 12. In one embodiment, the solid surface is selected from the group comprising a bead, a plate, or a slide. In one embodiment, the method results in an enriched population of pluripotent cells as compared to the mixture. In one embodiment, the method is performed during a reprogramming of the mixture of cells. In one embodiment, the method is performed on a patient sample. In one embodiment, the bead is a Dynal bead.

In one embodiment, a composition is described comprising an antibody and a cell preparation wherein the antibody is directed towards CD44, beta 2 microglobulin, endosialin, cadherin 11 or colectin 12. In one embodiment, the composition further comprises a solid support. In one embodiment, the cell preparation comprises a pluripotent cell, a differentiated cell or a partially reprogrammed cell or any combination thereof. In one embodiment, the composition further comprises an exogenously introduced reprogramming factor. In one embodiment the antibody is conjugated to a drug or other active agent capable of affecting the cell (i.e. affecting viability etc.).

In one embodiment, a method is described for diagnosis of the differentiation state of a cell, the method comprising identifying the expression level of a marker in a cell, the marker selected from the group consisting of CD44, beta 2 microglobulin, endosialin, cadherin 11 and colectin 12 and wherein the expression of the marker identifies the cell as a differentiated or partially differentiated cell or the lack of expression of the marker identifies the cell as a pluripotent cell. In one embodiment, the determined pluripotency (or partial or lack thereof) of a cell may correlate with a certain prognosis or a certain treatment regime. Such a correlation would be ascertainable and/or known by one of skill in the art.

In one embodiment, a method is described for enhancing reprogramming of a cell towards pluripotency, the method comprising the inhibition of the expression of a marker gene wherein the gene is selected from the group consisting of CD44, beta 2 microglobulin, endosialin, cadherin 11 and colectin 12. In one embodiment, the method further comprises introducing at least one reprogramming factor (i.e. nucleic acid, small molecule, protein etc.) into the cell. In another embodiment, differentiation (or loss of pluripotency) is induced or enhanced by expression of these marker genes.

In one embodiment, inhibition of gene expression can refer to inhibition of any step in the production of protein from a nucleic acid capable of encoding such a protein (or proteins).

In one embodiment, the ability to distinguish pluripotent (i.e fully reprogrammed or ESC or other stem cell types) from less pluripotent cells (i.e. partially reprogrammed or differentiated cell types) will be a critical step in methods known to one of skill in the art. Such embodiments are envisioned herein. In one embodiment, such methods include the administration of an agent to a cell preparation (or patient) and the analysis of the cell population (i.e. before and after administration) where that analysis can measure whether the agent affects the proportion of cells exhibiting a particular level of pluripotency (i.e. zero to full). In one embodiment, the agent is selected based on its ability to impact the activity of a marker identified herein.

In one embodiment, a kit is described for performing a method described herein, the kit comprising at least on element described as used in the method.

EXAMPLES

Example 1: Identification of a Differential Markers by Global Gene Expression Data Exemplary markers were identified by global transcriptome analysis of human fibroblast BJ cells (ATCC #CRL-2522) and their expression was compared to H9 ESC (WiCell) and CytoTune-generated iPSC reprogrammed cell lines, as shown below in Table 1.

| Surface protein | TargetID | Binds to | LifeTech Ab | AVG Signal-BJ | AVGSignal-H9 ESC on iMEF | AVGSignal-BS3C iPSC on iMEF | x upregulation over ESC | x upregulation over iPSC |
|---|---|---|---|---|---|---|---|---|
| Beta2 microglobulin | B2M | | Yes, against human | 37142 | 2308 | 1691 | 16 | 22 |
| Endosialin | CD248 | Collagen and fibronectin | | 13597 | 354 | 339 | 39 | 41 |
| CD44 | CD44 | Hyaluronic acid and other ligands, such as osteopontin collagens, and matrix metalloproteinases | Conj (incl biotin) | 8652 | 294 | 318.8 | 29 | 27 |
| Cadherin 11 | CDH11 | CDH2? | | 18365 | 822 | 488.1 | 22 | 41 |
| Colectin 12 | COLEC12 | Carbohydrates including Gal-type ligands, D-galactose, L- and D-fucose, GalNAc, T and Tn antigens in a calcium-dependent manner and internalizes | | 12256 | 1043 | 500.5 | 12 | 21 |

| Surface protein | TargetID | Binds to | LifeTech Ab | AVG Signal-BJ | AVGSignal-H9 ESC on iMEF | AVGSignal-BS3C iPSC on iMEF | x upregulation over ESC | x upregulation over iPSC |
|---|---|---|---|---|---|---|---|---|
| | | specifically GalNAc nurse-like cells. Binds also to sialyl Lewis X or a trisaccharide and asialo-orosomucoid (ASOR) | | | | | | |

The data was generated using human WG-6 v3.0 Bead-Chip Array (Illumina), and a few other markers that also showed differential expression were identified, and are listed above in Table 1. Markers that were differentially expressed in BJ fibroblasts (col. 5) compared to H9 ESCs (col. 6) and CyoTune-derived iPSC cell lines (col. 7) were beta 2 microglobulin, endosialin, CD44, cadherin 11 and colectin 12. These candidate markers showed >10 fold upregulation of each marker's expression when comparing it to BJ fibroblast expression. Of these, CD44 was of particular interest and was studied further as it was highly expressed in both human and mouse fibroblasts, and could easily be detected using the IM7 monoclonal antibody clone against CD44. CD44 showed about 29 fold more expression in BJ fibroblasts than in ESCs (col. 8), and about 27 fold more expression in BJ fibroblasts than in iPSCs (col. 9), making it an ideal marker to distinguish between pluripotent and non-pluripotent cells.

Example 2: Confirmation of the Differential Pattern of CD44 Expression in Parental Fibroblasts and iPSCs CD44 is highly expressed in human fibroblasts, a somatic cell type most commonly used as the parental cell type for reprogramming. Consequently, anti CD44 antibody (BD Pharminogen, Cat #550538 or Life Technologies Cat #RM5700) conjugated with AF 488 (Life Technologies, Cat #A11006) showed robust staining (FIG. 1a: left panel). In contrast, iPSC derived from BJ-fibroblast do not stain positive with anti-CD44-AF 488 although the edges of the colonies that are differentiated do show relatively higher labeling (FIG. 1a: right panel). FACS analysis of fibroblasts and iPSC stained with anti-CD44-AF488 showed a distinct separation of the robust positive BJ fibroblasts (with ~1000 arbitrary fluorescence units) and the negative iPSC (with <10 arbitrary fluorescence units-data not shown).

Figure 1B:
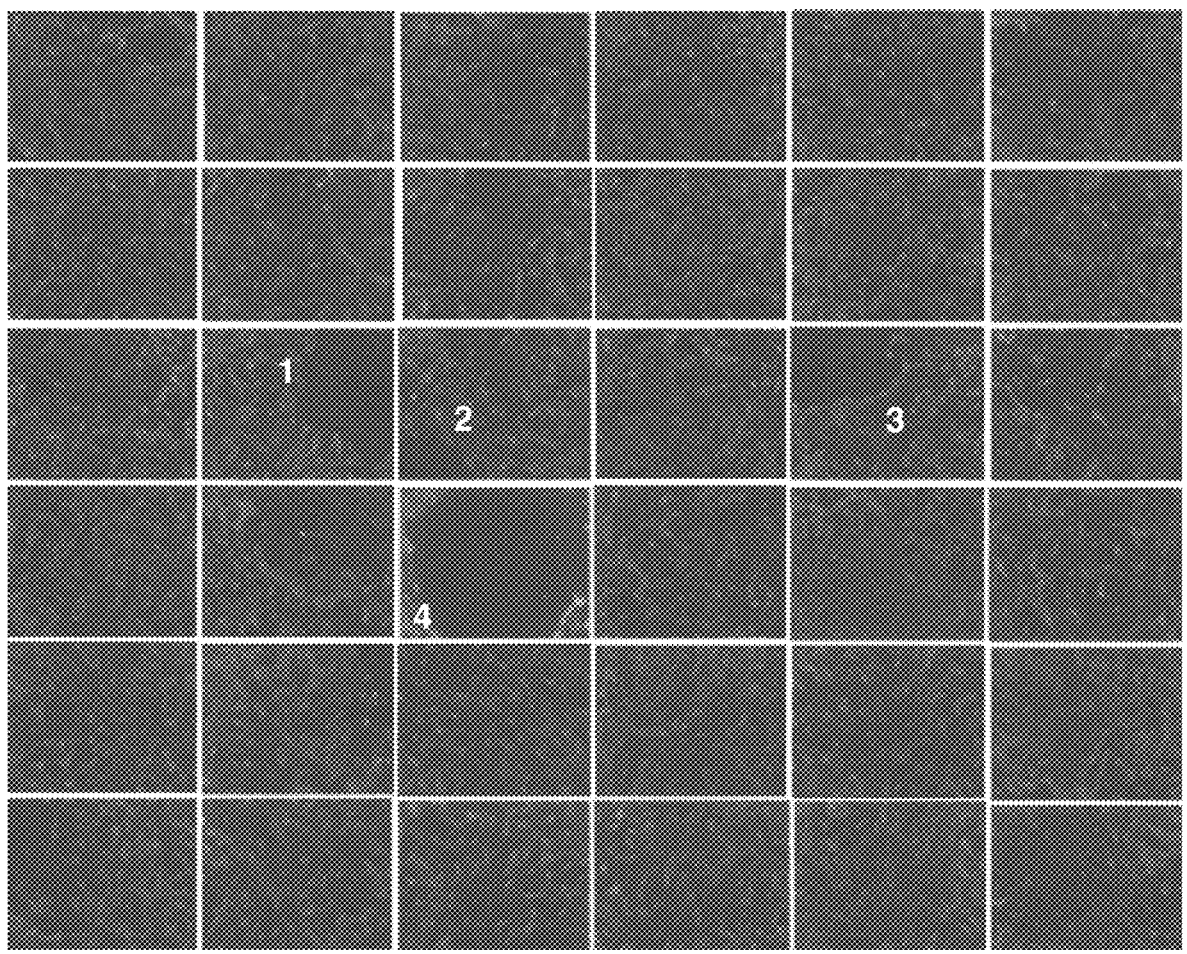
FIG. 1(B) shows the emergence of iPSCs in a lawn of CD44-AF488- positive cells (BJ fibroblasts) using a live monitoring system. BJ Human fibroblasts were reprogrammed with CytoTune, and cultured under feeder-free culture conditions.

FIG. 1(b) shows the reprogramming of parental fibroblasts and the visualization of the emerging iPSCs using a live monitoring system. Parental BJ human fibroblasts were reprogrammed with CytoTuner®-iPS reprogramming kit (Life Technologies, Cat #A1378001) under feeder-free culture conditions.

Cells were stained with anti-CD44-AF 488 antibody and 36 independent images were captured using the INCUCYTE™ live monitoring system (Essen BioScience, Michigan, USA). Emerging iPSCs, observed as dark holes within a lawn of CD44-AF488-positive cells (unreprogrammed and partially reprogrammed cells that stain positive for the CD44 marker), were marked with numbers 1, 2, 3, 4 on the images.

Figure 2:
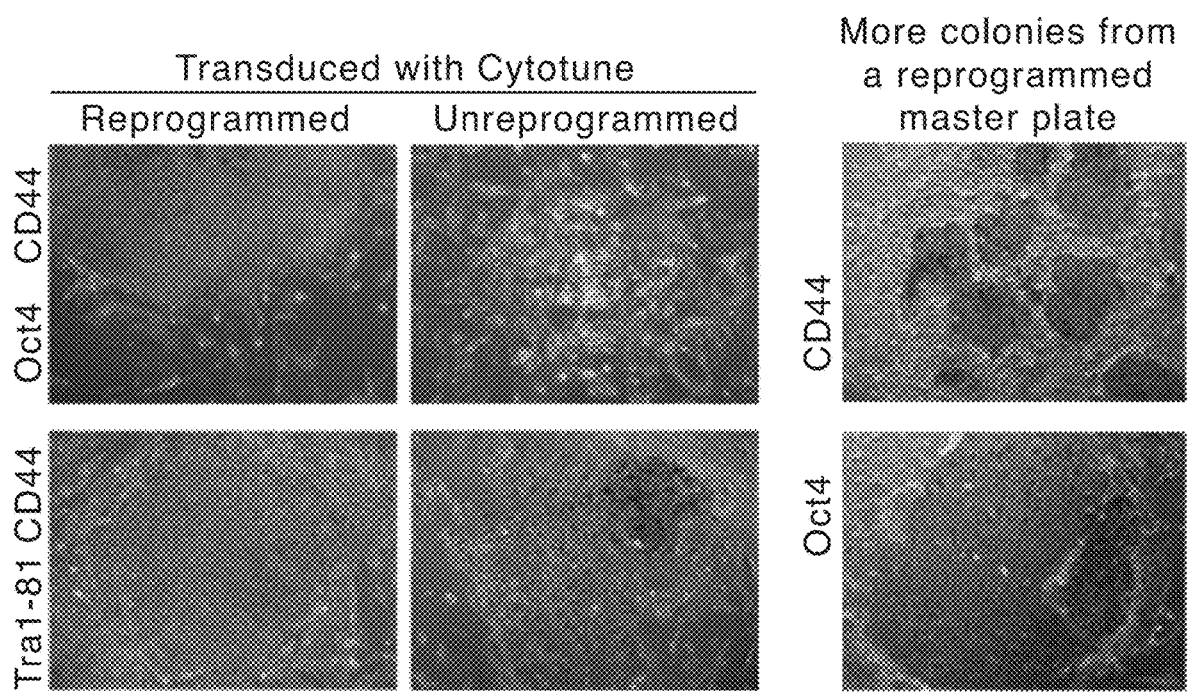
FIG. 2 shows that anti-CD44 antibody can distinguish between reprogrammed cells and partially reprogrammed cells. BJ fibroblasts were reprogrammed with the CytoTune™-iPS reprogramming kit and stained with anti-CD44-AF 488 antibody, and with two known pluripotent markers, Oct4 and Tra-1-81.

Example 3: CD44 can Distinguish Between Fully Reprogrammed Fibroblasts and Partially Reprogrammed Fibroblasts To further examine if CD44 can be utilized to distinguish unreprogrammed and partially reprogrammed cells from completely reprogrammed cells, BJ fibroblasts reprogrammed with CytoTune™-iPS reprogramming kit for 3 weeks were stained with anti-CD44-AF 488 antibody and with two known pluripotent markers, Oct4 (Life Technologies, Cat #A13998) and Tra-1-81 (Life Technologies, Cat #411100). FIG. 2 shows colonies with distinct ESC like morphology stained negative for CD44 and positive for the pluripotent specific markers. Interestingly, heterogeneous colonies show clear separation of the Oct4+/TRA1-81+/CD44− reprogrammed areas and Oct4+/TRA-1-81−/CD44+ unreprogrammed/partially reprogrammed cells. Dual staining of pluripotent specific antibody Oct4 or Tra-1-81 (red) and fibroblast specific CD44 (green) in BJ fibroblasts reprogrammed with CytoTune for 3 weeks.

Example 4: Utilization of Differential CD44 Expression to Separate Parent Fibroblasts from Pluripotent Stem Cells (iPSCs)

Figure 3:
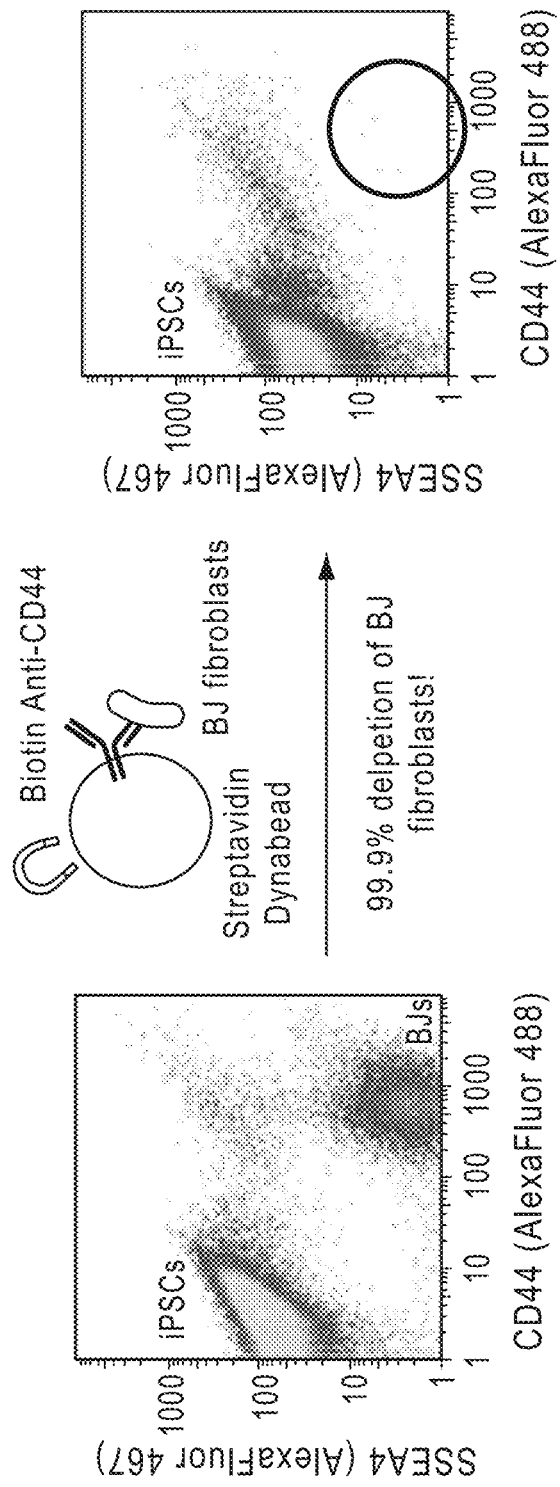
FIG. 3 shows that differential CD44 expression was utilized to separate a CD44+/SSEA4- BJ fibroblast population from a CD44-/SSEA4+iPSC population. Using an anti-CD44-biotin conjugated antibody system and Dynal® MyOne™ Streptavidin magnetic beads, 99% of the BJ fibroblasts were depleted from the iPSC enriched sample.

To provide proof of concept for utilization of CD44 differential expression in the reprogramming workflow, well-established iPSC clones were mixed with BJ human fibroblasts. These two cell populations showed clear separation by FACS analysis as seen in FIG. 3, where CD44+/SSEA4− BJ fibroblasts and CD44−/SSEA4+iPSC showed distinct scatter patterns (left panel). Following treatment of cells with anti-CD44 antibody coupled to biotin (BD Pharmingen, Cat #553132), incubation with Dynal® MyOne™ Streptavidin magnetic beads, and subsequently the antibody bound fraction was pulled down with a magnet. The remaining unbound fraction was removed in the supernatant and subjected to incubation with CD44 antibody conjugated to AF 488 and SSEA4-AF 647 antibody (Life Technologies, Cat SSEA4-421). As observed in FIG. 3, the CD44+/SSEA4-BJ fibroblast cell population was completely eliminated from the iPSC population with over a 99% removal percentage of fibroblast cells from a heterogeneous mixture of fibroblastic and iPSC cells.

Example 5: Confirmation of the Differential Pattern of CD44 Expression in Parental Fibroblasts and MEFs Murine Embryonic fibroblasts or MEFs are commonly used as feeders for feeder-dependent culture of pluripotent stem cells (PSC) such as human embryonic stem cells (ESC) and induced pluripotent stem cells (iPSC). The feeder-layer is mitotically inactivated with Mitomycin C or via irradiation so the cells do not proliferate but provide support to the growing PSC. In instances where MEF needs to be removed from the cultures, cells are passaged on to feeder-free conditions in the presence of MEF conditioned media for a generation to dilute out the residual MEF. This process adds time and variables to the culture and hence not ideal for certain applications. An appealing alternative would be physical removal of MEFs from the PSC culture to result in an enriched population of cells of interest that can then be utilized for downstream use or analysis. A tool that preferentially eliminates fibroblasts could also offer a valuable tool to remove parental fibroblasts during the process of somatic reprogramming. The intermediate steps during reprogramming consist of a combination of unreprogrammed parental fibroblasts, partially reprogrammed and completely reprogrammed cells. Markers that would discriminate the different stages will allow for elimination of the unwanted cells from the reprogrammed cells.

Figure 4A:
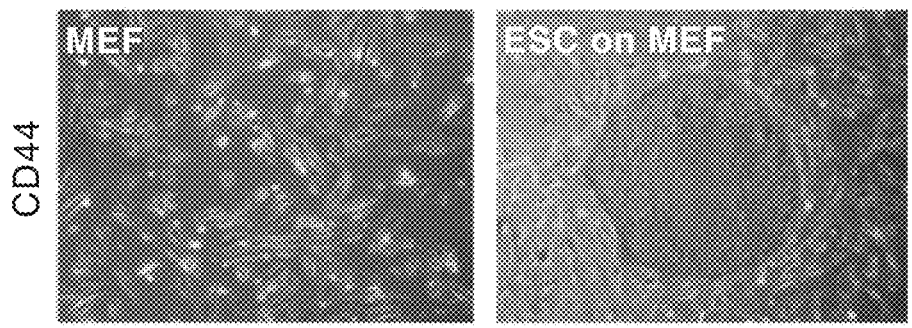
FIG. 4 provides experimental confirmation of the differential CD44 expression pattern between mouse embryonic fibroblast (MEF) feeders and iPSCs. Panel 4A) shows a CD44 antibody-AF488 staining of mouse embryonic fibroblasts (MEF) alone (left panel), and H9 ESCs cultured on MEFs (right panel). Panel 4B) shows results of a FACS analysis of CD44 antibody-AF488 stained MEF alone, and H9 ESCs cultured on MEF. There was good separation between MEFs and ESCs showing that CD44 is a good marker for distinguishing between these cells.
Figure 4B:
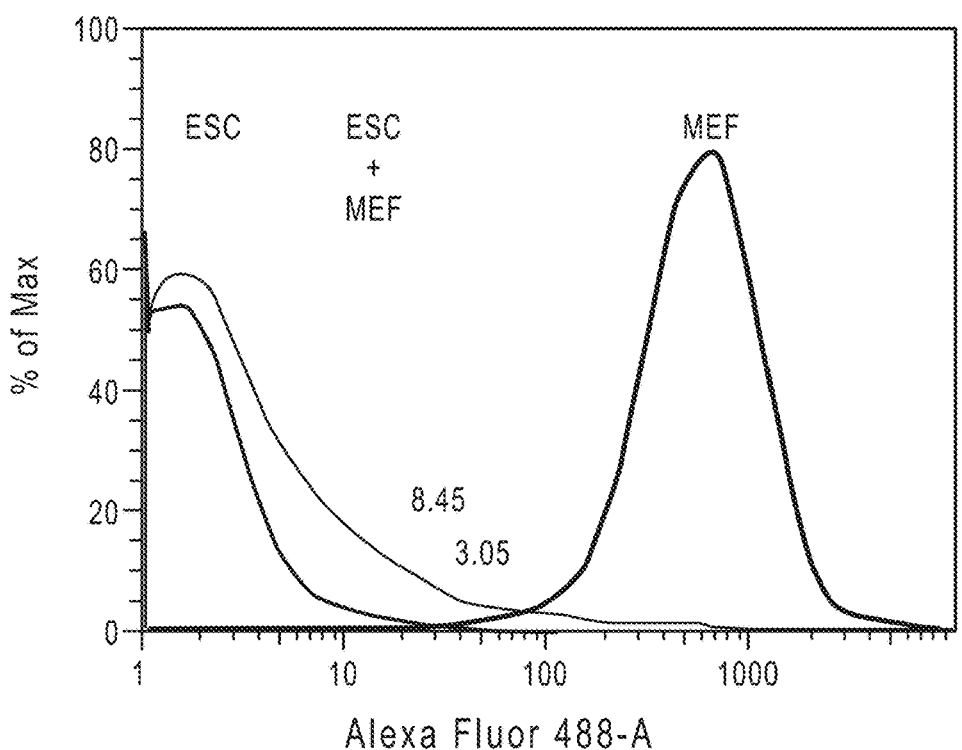

In order to test the pattern of CD44 expression in fibroblasts versus PSCs, anti-CD44 antibodies were coupled with secondary antibody tagged to AlexaFluor488, and were used to stain MEF feeder cells alone, and undifferentiated H9 ESCs cultured on MEF feeders. Robust expression was observed in MEFs while ESCs remains unstained (FIGS. 4a and b). MEF showed bright anti-CD44-AF488 signal (~1000 arbitrary fluorescence units) while ESC showed an absence of antiCD44-AF488 signal (<10 arbitrary fluorescence units).

Figure 5:
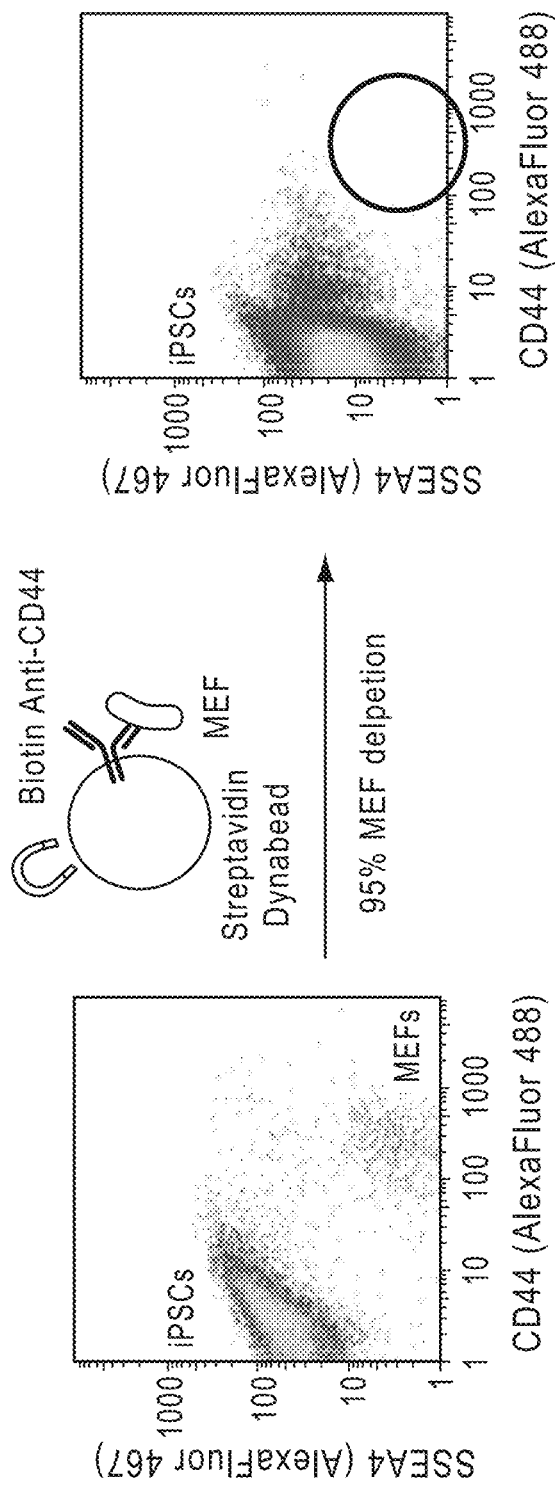
FIG. 5 shows the use of differential CD44 expression to separate MEFs from iPSCs. Using the anti-CD44-biotin conjugated antibody system and Dynal® MyOne™ Streptavidin magnetic beads, 95% of the mouse embryonic fibroblasts (MEFs) were depleted from the iPSC enriched sample.

Example 6: Utilization of Differential CD44 Expression to Separate PSCs from MEFs in Co-Culture Since CD44 was differentially expressed in MEFs and PSCs, use of an antibody or a ligand that bound to CD44 was used for the separation of MEFs from ESCs providing an easy and efficient way to separate ESCs from MEFs. This simple step negates the current practice of having to culture the cells under feeder-free conditions for 1-2 passages to dilute down the MEF feeders thus adding time and variability. Anti CD44 antibody conjugated to biotin in combination with DynalR, Streptavidin magnetic bead was used to successfully separate MEF from PSC via magnetic pull down of the Dynal® Streptavidin magnetic bead thus pulling down the bound CD44 expressing MEF away from the unbound PSC (FIG. 5). FACS scatter plot analysis further demonstrated the clear separation of CD44 stained MEFs (CD44+/SSEA4– MEFs) and ESC (CD44–/SSEA4+iPSCs), which were depleted over 90% following treatment with anti-CD44 antibody conjugated to biotin in combination with Dynal® Streptavidin magnetic beads, which was pulled down with a magnet (FIG. 5).

Example 7: Alternate Methods for Capturing CD44 on Fibroblasts

An additional advantage of generating a differential expression list is that specific markers of choice can be selected, such as surface markers for enrichment, genes specific to key pathways etc. With surface markers, besides antibodies specific to the markers, ligands may be utilized for the enrichment or depletion. For example, hyaluronic acid is known to bind to CD44. Hyaluronic acid can be used in solution or may be coated on surfaces to create a binding surface for trapping CD44 positive cells.

Figure 6:
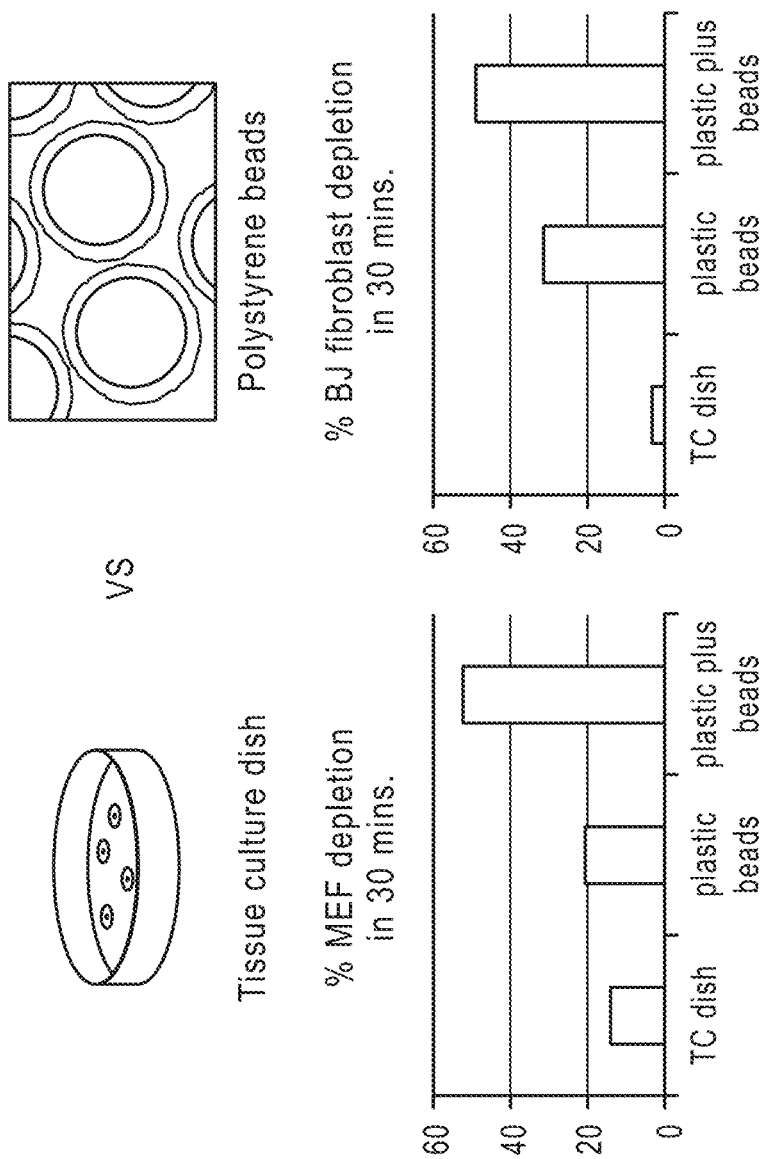
FIG. 6 demonstrates that based on CD44's affinity for ligands such as hyaluronic acid, antibody-free technologies can be developed to sequester and separate CD44 expressing cells (such as parental fibroblasts, MEFs) from non-CD44 expressors.

The relatively higher adherence of fibroblast to plastic can be harnessed to preferentially bind fibroblasts to eliminate them from co-cultures with ESC. This method achieves about <50% depletion thus necessitating multiple rounds of depletion (FIG. 6). Plastic dishes coated with CD44 antibody or hyaluronic acid (HA) can be used to increase this efficiency significantly (Experiments in progress). High adherence of fibroblasts may result in greater attachment of these cells to plastic surfaces or beads in a shorter period of time compared to ESCs, but may be achieved by less than 50%. This feature could be significantly enhanced by coating surface with CD44 antibody or more cost-effective method of using a CD44 ligand such as hyaluronic acid.

Figure 7:
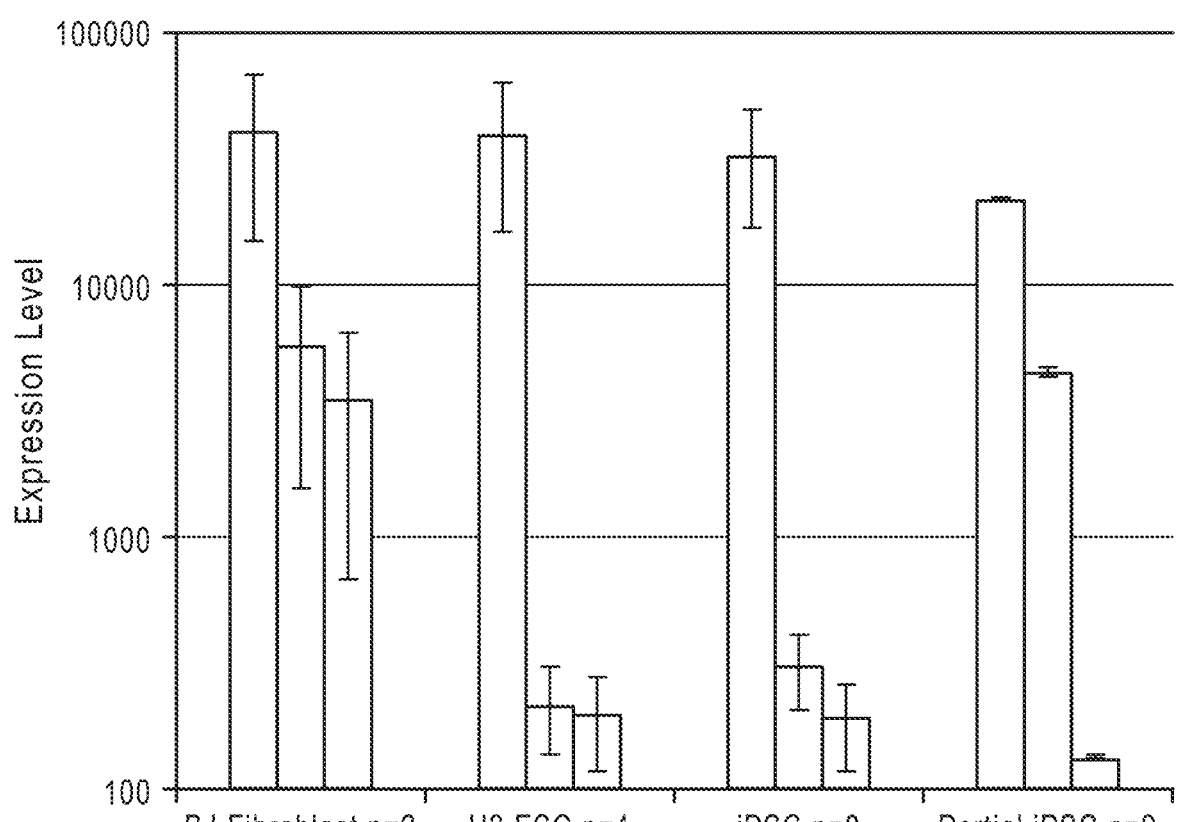
FIG. 7 shows comparative expression data from a Bead Array experiment for CD44 with other fibroblast markers such as CD13 (from New York Stem Cell Foundation (NYSCF)).
Figure 8A:
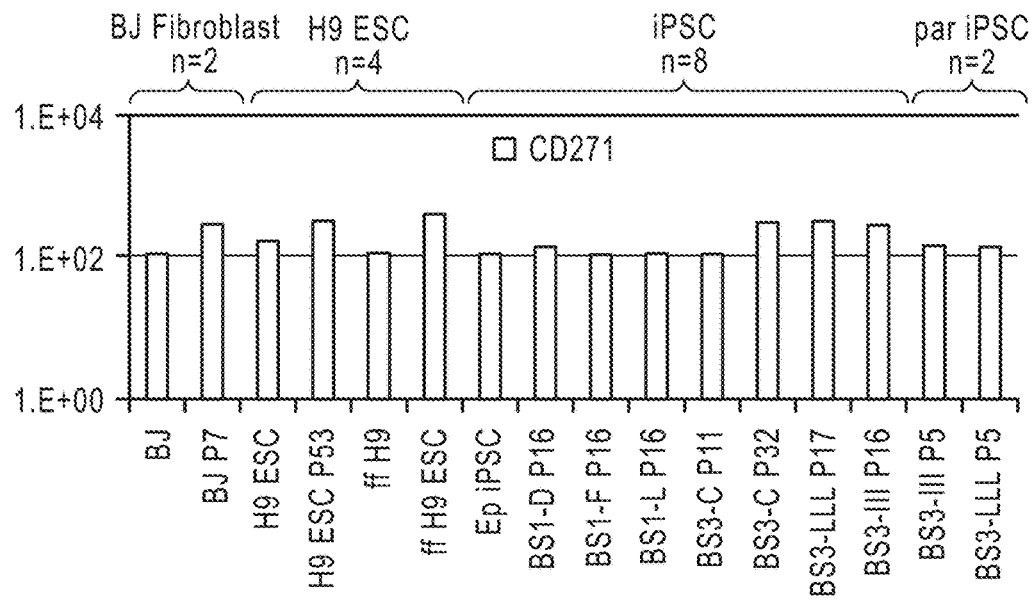
FIGS. 8A-8B show that comparative expression data for CD44 and another fibroblast marker, CD271 (Miltenyi Biotec, Germany), which was obtained b another bead array experiment. CD271 marker is commercially available and is used in human anti-fibroblast microbeads to separate human fibroblasts in a mixture of cells.
Figure 8B:
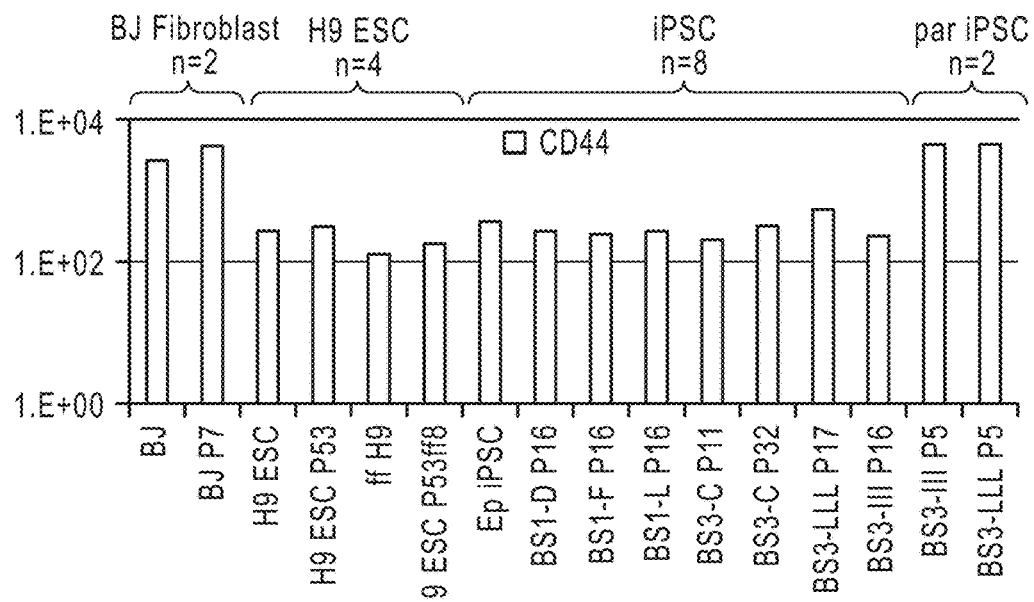

Example 8: Comparison of CD44 Expression with Other Mesenchymal-Specific Markers Gene expression from multiple samples were grouped into the following four categories: (1) parental human fibroblasts (negative control) (n=2); (2) H9 ESC (positive control) (n=4); (3) true iPSC clones (n=8, 7 CytoTune-derived+1 episomal-derived)–passed the cellular criteria and the PluriTest; and, (4) partially reprogrammed clones (n=2)–failed the PluriTest and did not form EBS (embryoid bodies). Differential expression of well known pluripotent markers such as alkaline phosphatase (ALPL) and E-cadherin (CDH1) were analyzed and compared to housekeeping gene ACTB-beta actin expression (control) amongst parental cells, partially reprogrammed and fully reprogrammed cells. They were included to demonstrate the expression of high levels of these transcripts in pluripotent ESC and iPSC lines but not in the negative control or partially reprogrammed cells. Since CD44 is also a known mesenchymal marker, other mesenchymal/fibroblast markers such as CD90 and CD13 were also analyzed (Table 2). High expression is marked in red. As seen from Table 2 and FIG. 7, CD44 expression (red bar) is high, not only in parental BJ fibroblasts, but also in partially reprogrammed iPSCs, but is low in completely reprogrammed iPSCs and in the positive control, the H9 ESC cell. Therefore, compared to other mesenchymal markers like CD13 and CD90, CD44 is a preferred marker to clearly help distinguish between partial pluripotency and complete pluripotency.

Table 2: Expression levels of known pluripotent and mesenchymal markers in grouped samples as shown below.

|  | Sample | House Keeping ACTB | Pluripotent | | Non-Pluripotent Mesenchymal specific | | |
| --- | --- | --- | --- | --- | --- | --- | --- |
|  |  |  | ALPL | CDH1 | CD13 | CD44 | CD90 |
| Negative Control | BJ | 22667 | 168 | 117 | 1530 | 2748 | 8302 |
| Human Fibroblast | BJ P7 | 60036 | 431 | 187 | 5665 | 8652 | 1469 |
| Positive Control | H9 ESC | 23043 | 4943 | 989 | 130 | 280 | 1693 |
| H9 ESC | H9 ESC P53 | 59895 | 7500 | 4633 | 253 | 294 | 2474 |
|  | ff H9 | 16046 | 2858 | 4017 | 126 | 118 | 2180 |
|  | Ff H9 ESC P53ff8 | 61756 | 7881 | 9107 | 283 | 189 | 2280 |
| Completely Reprogrammed | Ep iPSC | 22214 | 5078 | 2355 | 134 | 370 | 2015 |
| iPSC | BS1-D P16 | 22015 | 5808 | 3591 | 146 | 286 | 2259 |
|  | BS1-F P16 | 19887 | 6203 | 3596 | 142 | 240 | 2414 |
|  | BS1-F P16 | 21287 | 6518 | 3236 | 127 | 255 | 2101 |
|  | BS3-C P11 | 21280 | 3477 | 3235 | 146 | 204 | 2008 |

-continued

|  | Sample | House Keeping ACTB | Pluripotent ALPL | Pluripotent CDH1 | Non-Pluripotent Mesenchymal specific CD13 | Non-Pluripotent Mesenchymal specific CD44 | Non-Pluripotent Mesenchymal specific CD90 |
|---|---|---|---|---|---|---|---|
|  | BS3-C P32 | 57159 | 9239 | 8555 | 237 | 319 | 1419 |
|  | BS3-LLL P17 | 49472 | 15376 | 21542 | 289 | 523 | 113 |
|  | BS3-III P16 | 50444 | 20565 | 24226 | 281 | 254 | 1097 |
| Partially Reprogrammed | BS3-III PS | 21762 | 226 | 108 | 137 | 4640 | 112 |
| iPSC | BS3-LLL PS | 22483 | 193 | 101 | 132 | 4493 | 1076 |

CD13 marker (see U.S. appl. No. US2011/0306516) has been used as a depletion marker to remove un-reprogrammed cells in combination with positive pluripotent markers by FACS sorting. However, as seen from Table 2 and FIG. 7, CD13 does not seem to distinguish well between partially reprogrammed and fully reprogrammed iPSC cells. While CD13 does not seem to distinguish between partially reprogrammed iPSC and fully reprogrammed cells (FIG. 7, blue bars), CD44 seems to distinguish between the two discrete states (FIG. 7, red bars) thereby providing a better handle to identify and select bonafide iPSC clones. US2011/0306516 describes CD13 in combination with TRA for specific enrichment of reprogrammed cells. Based on gene expression data analysis, CD13 is not differentially expressed between partially reprogrammed and reprogrammed cells.

Another commercially available product from Miltenyi Biotec is specific only for fibroblasts and does not distinguish between partially and fully reprogrammed cells. One of the anti Fibroblast microbeads (Miltenvibiotec #1 30-050-60 1) is a specific for a known fibroblast marker LNG FR (CD271), that is also a well known MSC marker utilized for its isolation from bone marrow. (Jones, E. A. et al. (2007) Purification of proliferative and multipotential marrow stromal cells (MSCs) from bone marrow aspirate by selection for CD271 (LNGFR) expression. *MACS & more* 11-1: 22-25).

Figure 9:
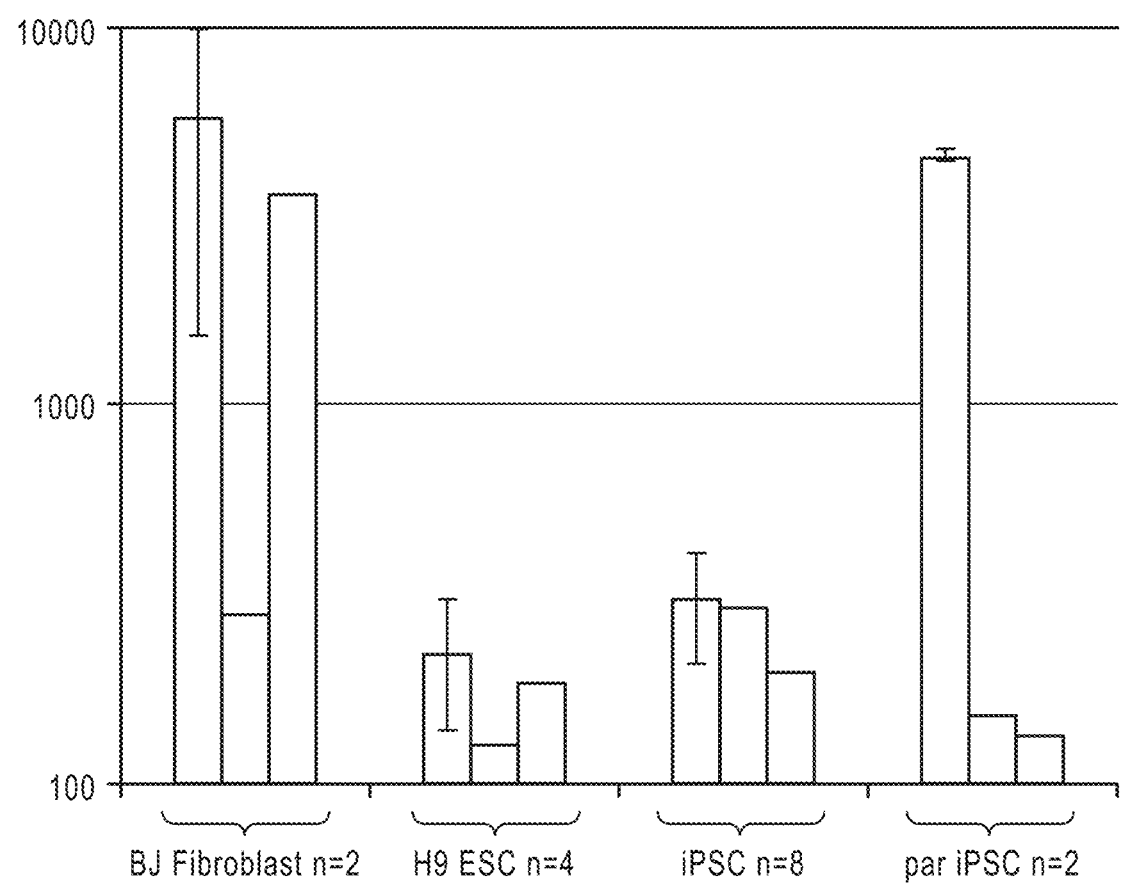
FIG. 9 shows the summary of comparative expression data for CD44 (left bar), CD 13 (middle bar) and CD271 (right bar) in various cells.
Figure 10:
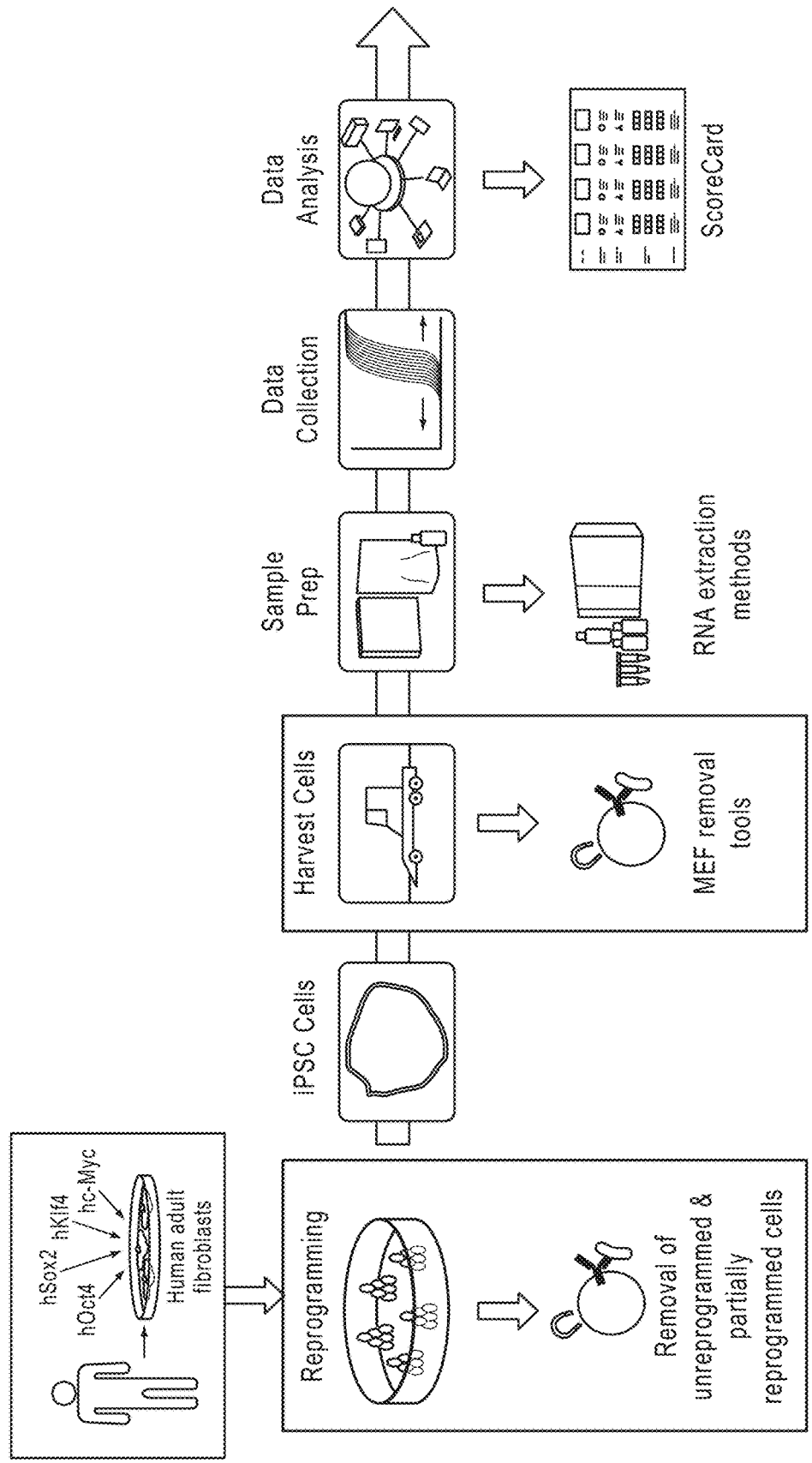
FIG. 10 shows an exemplary use of the markers identified in this disclosure in a typical stem cell workflow.
Figure 11A:
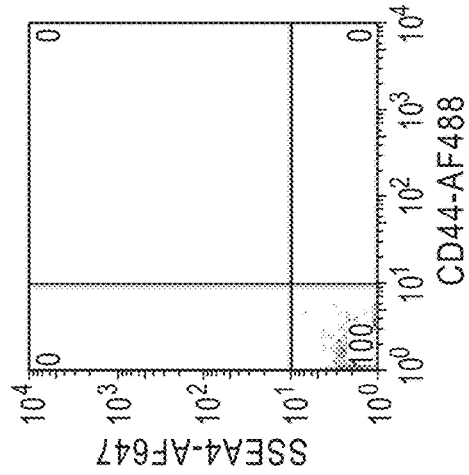
FIG. 11: FACS analysis of BJ shows high expression of CD44 and absence of SSEA4 while the pluripotent control H9 ESC cultured under feeder-free condition show presence of the pluripotent SSEA4 and absence of CD44 marker. BJ fibroblasts reprogrammed with CytoTune for 26 days shows a combination of SSEA4+/CD44-, SSEA4+/CD44+ and SSEA4-/CD44+ population of cells. Following depletion of the control H9 ESC and the BJ reprogrammed cells, the CD44 population is eliminated from the BJ reprogrammed cells without altering the SSEA4 positive population in the control ESC and the BJ reprogrammed cells. The enrichment of the SSEA4 positive cells and elimination of CD44 population in reprogramming fibroblasts allows selection of the desired population for further expansion and downstream application. Panel 11(A) depicts unstained BJ fibroblasts. Panel 11(B) depicts unstained H9 ESC. Panel 11(C) depicts unstained reprogrammed fibroblasts (i.e. fibroblasts subjected to 26 days of reprogramming). Panel 11(D) depicts stained undepleted BJ fibroblasts. Panel 11(E) depicts stained undepleted H9 ESC. Panel 11(F) depicts stained undepleted reprogrammed fibroblasts (i.e. fibroblasts subjected to 26 days of reprogramming). Panel 11(G) depicts stained H9 cells that have been subjected to targeted depletion against CD44. Panel 11(H) depicts stained reprogrammed fibroblasts (i.e. fibroblasts subjected to 26 days of reprogramming) that have been subjected to targeted depletion against CD44.
Figure 11B:
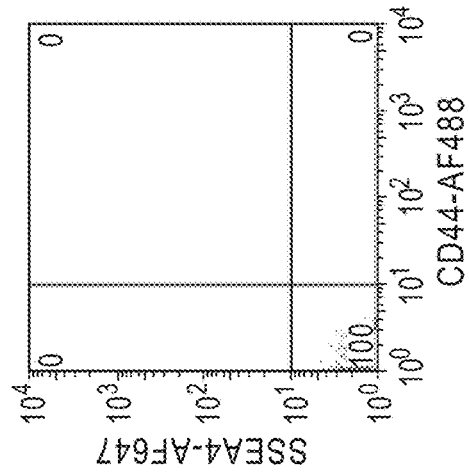
Figure 11C:
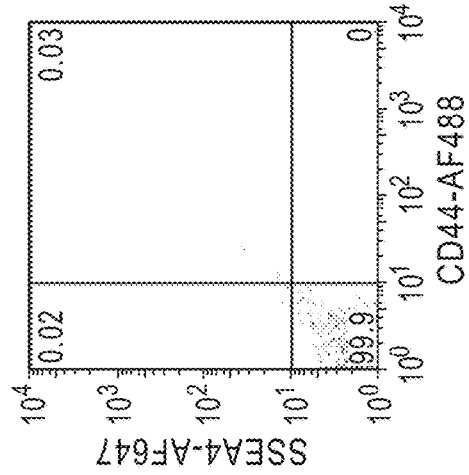
Figure 11D:
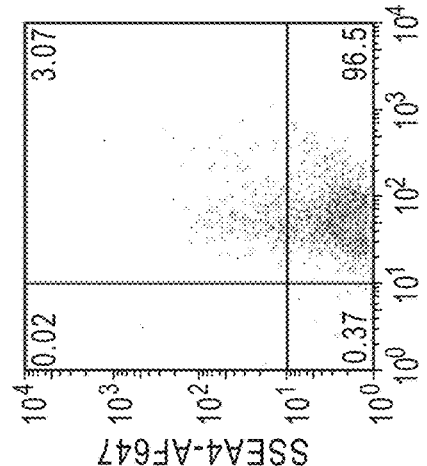
Figure 11E:
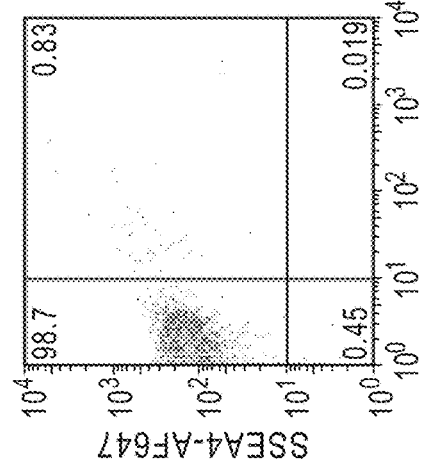
Figure 11F:
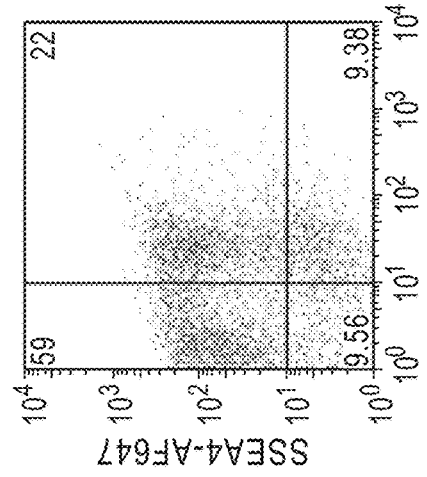
Figure 11G:
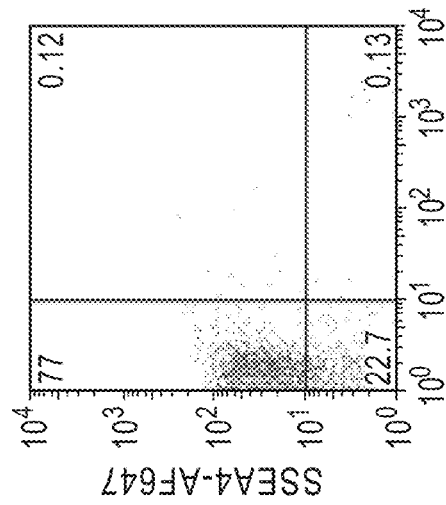
Figure 11H:
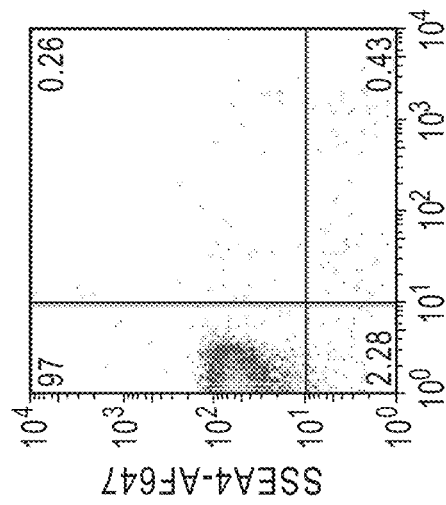

Whole gene expression data generated from parental human fibroblasts (black bar), pluripotent ESC (blue bar) and iPSC clones (pink bar) that were confirmed to be pluripotent and clones that expressed pluripotency but failed to differentiate thus constituting partially reprogrammed cells (orange bar) was used to determine the transcript levels of the markers currently used for fibroblast detection. This suggests that although CD271 maybe a good marker for MSC isolation, it is not for the iPSC workflow and its features do not compete with CD44. Similarly, the mouse Feeder removal Microbeads from Miltenyi Bitotec (Miltenyibiotec #130-095-531) is a mouse specific marker with intended use of removal of murine embryonic fibroblast feeder cells from feeder-dependent ESC and iPSC cultures. It does not compete with CD44 since it is species specific to mouse and not applicable to human cells. A summary of the comparative expression of three fibroblastic markers CD44. CD271 and CD13 is shown in FIG. 9. While CD44 was highly expressed in MEFs, parental cells and partially reprogrammed cells, it was poorly expressed in PSC, thus making in an ideal marker to differentiate, both, between MEF feeder cells and pluripotent cells, as well as between partially reprogrammed cells and fully reprogrammed cells. On the other hand, fibroblast markers CD271 and CD13 failed to clearly differentiate between partially reprogrammed cells and fully reprogrammed cells as seen in FIG. 9. Therefore, this property of CD44 of identifying pluripotency over other cells like MEFs, parental cells and partially reprogrammed cells meets an unmet need in the workflow of a stem cell researcher/user.

The examples were intended to illustrate, but not limit, certain embodiments of the disclosure. One skilled in the art will understand that various modifications are readily available and can be performed without substantial change in the way the invention works. All such modifications are specifically intended to be within the scope of the invention claimed herein.

What is claimed is:

1. A method for identifying differentiated cells or partially reprogrammed cells within a mixture of differentiated, partially reprogrammed and pluripotent cells, the method comprising:
   contacting a mixture of differentiated, partially reprogrammed and pluripotent cells with a detectably labeled antibody wherein the detectably labeled antibody binds to differentiated cells or partially reprogrammed cells but does not bind to pluripotent cells;
   detecting the distinguishably detectable labeled antibody bound to the differentiated or partially reprogrammed cells;
   identifying the differentiated cells or the partially reprogrammed cells based on the detectably labeled antibody binding thereto and identifying the pluripotent cells based on a lack of the detectably labeled antibody binding thereto;
   wherein the detectably labeled antibody binds to one of CD44, beta 2 microglobulin, endosialin, cadherin 11 or colectin 12 expressed on cells and bound cells in the mixture are identified as the differentiated cells or partially programmed cells.

2. The method according to claim 1, wherein the cell is a mammalian cell.

3. The method according to claim 1, wherein the detectably labeled antibody binds to CD44.

4. The method according to claim 1, wherein the detectable label comprises a fluorescent dye, biotin, or live stain.

5. The method according to claim 1, wherein the proportion of differentiated cells or partially reprogrammed cells to pluripotent cells in the mixture of cells is determined.

6. The method according to claim 1, wherein the method is performed on a reprogrammed mixture of cells.

7. A method for determining the differentiation state of a cell, the method comprising:
   contacting a cell with a detectably labeled antibody which binds a marker selected from the group consisting of CD44, beta 2 microglobulin, endosialin, cadherin 11 and colectin 12;
   detecting the expression level of the marker in a cell, wherein the expression of the marker identifies the cell as a differentiated or partially differentiated cell and the lack of expression of the marker identifies the cell as a pluripotent cell.

8. The method according to claim 7, wherein the detectable label comprises a fluorescent dye, biotin, or live stain.

9. The method according to claim 7, wherein the detectably labeled antibody binds to CD44.

10. The method according to claim 7, wherein the cell is a mammalian cell.

11. The method according to claim 7, wherein the cell had been subjected to a reprogramming workflow.

* * * * *